US008062297B2

(12) United States Patent
Faillace et al.

(10) Patent No.: US 8,062,297 B2
(45) Date of Patent: Nov. 22, 2011

(54) BONE FIXATION APPARATUS AND METHOD OF MANUFACTURE

(75) Inventors: John Faillace, Temple, TX (US); David V. Mrak, North Street, MI (US)

(73) Assignee: BioPro, Inc., Port Huron, MI (US)

( * ) Notice: Subject to any disclaimer, the term of this patent is extended or adjusted under 35 U.S.C. 154(b) by 508 days.

(21) Appl. No.: 12/178,751

(22) Filed: Jul. 24, 2008

(65) Prior Publication Data

US 2010/0023062 A1 Jan. 28, 2010

(51) Int. Cl.
A61B 17/56 (2006.01)
A61B 17/58 (2006.01)
A61B 17/064 (2006.01)
A61B 17/84 (2006.01)
A61F 2/30 (2006.01)

(52) U.S. Cl. ........................................................ 606/75
(58) Field of Classification Search .................... 606/75, 606/219, 220, 297, 327
See application file for complete search history.

(56) References Cited

U.S. PATENT DOCUMENTS

| | | | |
|---|---|---|---|
| 4,170,990 A | 10/1979 | Baumgart et al. | |
| 4,946,468 A | 8/1990 | Li | |
| 5,474,557 A * | 12/1995 | Mai | 606/78 |
| 5,779,707 A | 7/1998 | Bertholet et al. | |
| 5,947,999 A * | 9/1999 | Groiso | 606/219 |
| 6,007,539 A | 12/1999 | Kirsch et al. | |
| 6,200,330 B1 | 3/2001 | Benderev et al. | |
| 6,325,805 B1 | 12/2001 | Ogilvie et al. | |
| 6,336,928 B1 | 1/2002 | Guerin et al. | |
| 6,685,708 B2 | 2/2004 | Monassevitch et al. | |
| 6,773,437 B2 | 8/2004 | Ogilvie et al. | |
| 6,783,531 B2 | 8/2004 | Allen | |
| 6,966,911 B2 | 11/2005 | Groiso | |
| 6,969,391 B1 | 11/2005 | Gazzani | |
| 2002/0156477 A1 | 10/2002 | Knopfle et al. | |
| 2003/0032981 A1* | 2/2003 | Kanner et al. | 606/219 |
| 2005/0010228 A1 | 1/2005 | Medoff | |
| 2005/0049600 A1 | 3/2005 | Groiso | |
| 2005/0096660 A1 | 5/2005 | Allen | |
| 2005/0273108 A1 | 12/2005 | Groiso | |
| 2005/0283159 A1 | 12/2005 | Amara | |
| 2006/0058802 A1 | 3/2006 | Kofoed | |
| 2006/0142771 A1 | 6/2006 | Beutter | |

OTHER PUBLICATIONS

For Fusion, "Lukewarm shape memory implant", http://us.nnemometal.com/us/ForFusion/24.html, accessed on Aug. 8, 2007, 2 pages.

* cited by examiner

*Primary Examiner* — Thomas C. Barrett
*Assistant Examiner* — Sameh Boles
(74) *Attorney, Agent, or Firm* — Brooks Kushman P.C.

(57) ABSTRACT

A bone fixation apparatus comprising a shape memory effect material includes a bridge member having at least three sides and an open center portion. Each of the bridge member sides defines a curve having a respective first radius when the shape memory effect material is in a first state, and a respective second radius larger than a corresponding first radius when the shape memory effect material is in a second state. Elongate members are connected to, and extend outwardly from, the bridge member. Each of the elongate members are connected to the bridge member at an approximate intersection of a respective two of the sides, such that each elongate member is subject to a force from each of two intersecting sides, and moves toward the open center portion of the bridge member when the shape memory effect material changes from the second state to the first state.

8 Claims, 3 Drawing Sheets

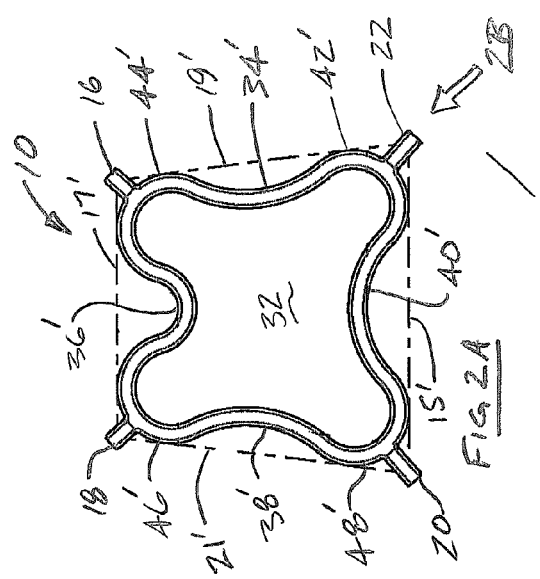
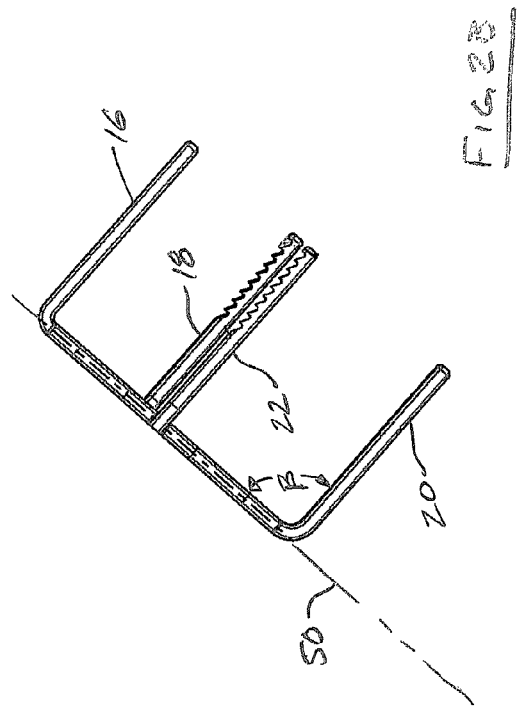
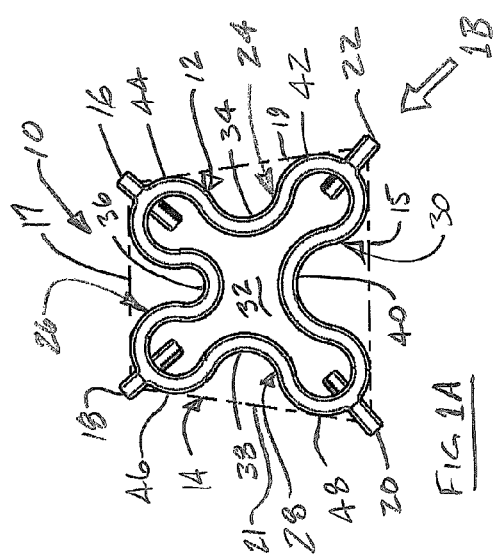
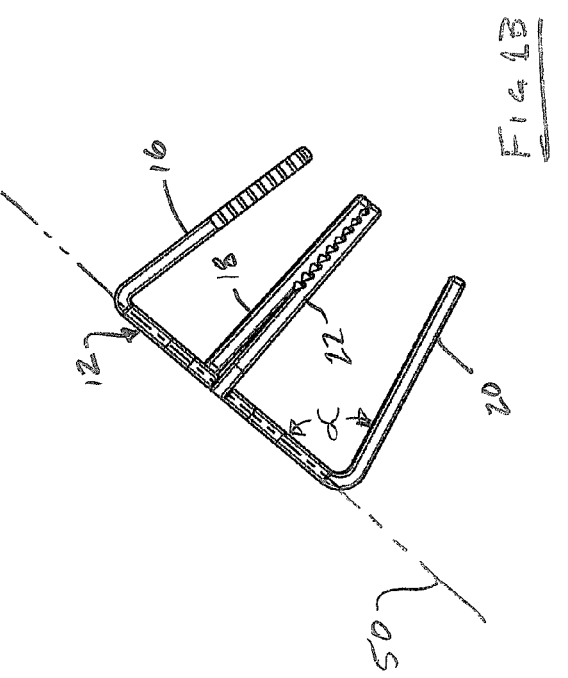

BONE FIXATION APPARATUS AND METHOD OF MANUFACTURE

BACKGROUND OF THE INVENTION

1. Field of the Invention

The present invention relates to a bone fixation apparatus and a method of manufacturing a bone fixation apparatus.

2. Background Art

The use of shape memory effect materials is known in a variety of fields. Devices made from shape memory effect materials are typically configured with a particular geometry at a first temperature, the temperature of the device is changed and the geometry is reconfigured, and then when the device is brought back to the first temperature, it regains its original geometry. One such shape memory effect material is nitinol, an alloy of titanium and nickel. Depending on the particular makeup of the alloy, it may have an austenitic microstructure at room temperature, and a martensitic microstructure at a lower temperature. In the martensite phase, a nitinol device is relatively soft and easy to deform. Upon returning to a warmer temperature, the device regains its original shape and becomes much stiffer as the microstructure transforms into austenite.

Nitinol has been used in the medical field for a number of different types of devices, for example, stents. The field of orthopedics is another area where nitinol devices have proved useful. In particular, bone staples made from nitinol have been used to stabilize fractured bones through the course of healing. In addition to holding the bone fragments in place, a nitinol staple can apply compression to the bone fragments to further aid in the healing process. One limitation of many of these types of devices is that they pull the bone fragments together in a straight line. Even when configured with more than two prongs, conventional bone staples are configured to pull two pieces of bone together at a single fracture line. Unfortunately, many bone fractures are not along a single fracture line, but rather, may have two or more fractures at or near one location. Moreover, in the case of a wrist or ankle, there are many small bones disposed close to each other, and, in a given situation, it may be necessary to pull three or four of these together toward a central location.

Therefore, a need exists for a bone fixation apparatus comprising a shape memory effect material that has a specific geometric configuration effective to pull three or more bone pieces together at or near a single location.

SUMMARY OF THE INVENTION

Embodiments of the present invention provide a bone fixation apparatus and a method for manufacturing such an apparatus that includes a bridge member having at least three tines extending outwardly therefrom. The tines are configured for insertion into bone pieces, and the bridge member is specifically configured to pull the tines inward toward a central portion of the bridge member. It is understood that the tines moving toward the central portion of the bridge member may or may not move toward an exact geometric center of the bridge member, but rather generally move toward the center because of forces applied by the sides of the bridge member.

Such a bridge member may form a generally planar, closed geometric figure that can be, for example, circumscribed by a polygon. To bring together at least three pieces of bone, the bridge member has at least three sides that correspond to the sides of the circumscribing polygon. Each of the bridge member sides is configured with a curve that has a respective first radius when the shape memory effect material from which the bridge member is made is in a first material state. The first material state will generally correspond with a first temperature or first temperature range. The bridge member is configured such that the curve in each of the bridge member sides has a respective second radius larger than a corresponding first radius when the shape memory effect material is in a second material state, generally corresponding to a second temperature or temperature range. The tines may be located at an approximate intersection of adjacent pairs of the sides. Thus, when the device transitions from the second material state, where the side curves have a larger radius, to the first material state, forces applied to the tines from each of the adjacent pairs of sides, moves the tines toward each other and toward an open center portion of the bridge member.

In practice, when such a bone fixation apparatus is implanted, there may be very little movement of the tines, since they will be constrained by the bones. However, the tines will then apply a force to the bones into which they are implanted, thereby bringing the bones together, or at least applying a force to the bones at the fracture site. The tines may be implanted by drilling corresponding holes in the bone pieces, into which the tines are hand pressed. The tines may also be configured with one or more serrated edges to aid in gripping the bone.

Embodiments of the invention include a bridge member and a plurality of tines as described above, where each of the curves defined by the bridge member sides curve inward toward an open center portion of the bridge member. The bridge member has an open center portion which, among other things, allows the fracture site to be viewed by x-rays during the healing process. In this way, a doctor knows whether healing is occurring properly, or if other measures are warranted. Embodiments of the invention also include a bridge member wherein the intersection of each pair of adjacent sides forms a respective intersection curve that, relative to the open center portion, curves in a direction opposite that of the curves defined by the bridge member sides.

Embodiments of the invention also provide for the tines comprising a shape memory effect alloy, such that in the second material state, the tines may be generally perpendicular to a plane that includes the bridge member; whereas, in the first material state, the tines are oblique to such a plane, and generally angled inward toward the open center portion of the bridge member. Embodiments of the invention may include a bridge member having four sides, and which may be circumscribed by a square, or in some embodiments, a trapezoid. A trapezoidal shaped device may be particularly effective for repairing fractures, or fusing, bones in the wrist.

Embodiments of the invention also include a method for manufacturing a bone fixation apparatus, such as the apparatus described above. The method includes such steps as wire electrical discharge machining (EDM) a shape memory effect material to form a generally planar, closed geometric figure having at least three sides and an open center portion. At least a portion of each of the sides is configured to define a curve that is curved inward toward the open center portion. A plurality of elongate members integral with and in a plane containing the generally planar, closed geometric figure are also formed using wire EDM. Each of the elongate members is formed such that it intersects the generally planar, closed geometric figure at an approximate intersection of a respective two of the sides.

The manufacturing method also includes bending each of the elongate members to extend outwardly from the plane containing the generally planar, closed geometric figure. In certain embodiments, the elongate members may be bent inward at an oblique angle to a plane containing the generally planar, closed geometric figure, such that each of the elongate members angles inward toward the open center portion. At some temperature below room temperature, the elongate members can be bent back—i.e., straightened—such that they are generally perpendicular to the plane containing the generally planar, closed geometric figure. In addition, the generally planar, closed geometric figure can be expanded such that the open center portion increases in area. Inserting such a device into a bone when it is in this second temperature-dependent, material state, facilitates the application of forces to the various bone pieces by the device as its temperature increases toward 37° C., and the material transitions into the first temperature-dependent, material state.

Embodiments of the present invention can be used in a variety of medical applications, for example, stabilizing bones that have more than one fracture line. Some applications include a scaphoid, trapezium, trapezoid (STT) fusion of the wrist, or in some more rare cases, a radio-scapho-lunate fusion. Embodiments of the present invention may also be effective for such applications as a metatarsal phalengeal (MTP) fusion, or a calcaneo-cuboid fusion and tarsal metatarsal fusion, although other applications are contemplated.

BRIEF DESCRIPTION OF THE DRAWINGS

FIG. 1A is a top plan view of an embodiment of a bone fixation apparatus in a first material state, in accordance with the present invention;

FIG. 1B shows a side plan view of the bone fixation apparatus shown in FIG. 1A in the direction of the arrow labeled 1B;

FIG. 2A is a top plan view of the bone fixation apparatus shown in FIG. 1A when it is in a second material state;

FIG. 2B is a side plan view of the bone fixation apparatus shown in FIG. 2A in the direction of the arrow labeled 2B;

DETAILED DESCRIPTION OF THE PREFERRED EMBODIMENT(S)

Figure 3:
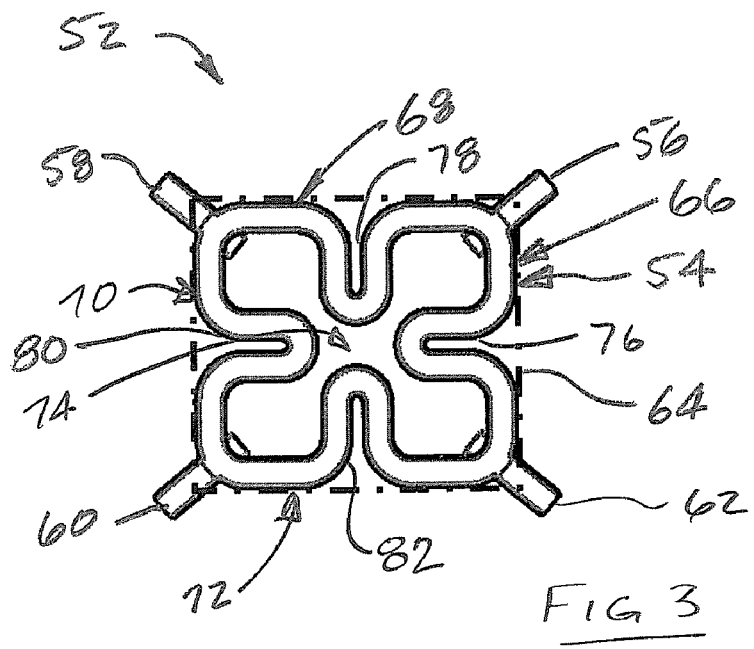
FIG. 3 is a top plan view of another embodiment of a bone fixation apparatus in accordance with the present invention.

FIG. 1A shows a bone fixation apparatus 10 in accordance with one embodiment of the present invention. The bone fixation apparatus 10 includes a bridge member 12 that forms a generally planar, closed geometric figure. As shown in FIG. 1A, the bridge member 12 is circumscribed by a trapezoid 14 that has a base 15, a top 17, and two legs 19, 21. The bone fixation apparatus 10 may be conveniently referred to as a bone staple; however, unlike conventional two-pronged staples, the bone staple 10 includes four elongate members or tines 16, 18, 20, 22.

The tines 16-22 of the bone staple 10 are disposed at the intersections of adjacent sides 24, 26, 28, 30 of the bridge member 12. Each of the bridge member sides 24-30 corresponds to a respective side 15-21 of the circumscribing trapezoid 14. As shown in FIG. 1A, the sides 24-30 of the bridge member 12 surround an open center portion 32. Having an open center portion, such as the center portion 32, provides advantages over bone staples having a solid bridge member.

The open center portion 32 allows a physician to observe the fracture or fusion site—e.g., by taking x-rays—throughout the healing process. In this way, the physician will be able to determine if the healing process is progressing appropriately, or whether additional remedial measures need to be taken.

Each of the bridge member sides 24-30 includes a respective curved portion 34, 36, 38, 40. In the embodiment shown in FIG. 1A, the radii 34, 38 of the bridge member sides 24, 28, have a larger radius than the curve 36 of the bridge member side 26 that corresponds to the top 17 of the trapezoid 14. Conversely, the curve 40 on the bridge member side 30 corresponding to the base 15 of the trapezoid 14 has a radius that is the largest of the four curves 34-40. As described in detail below, the curved bridge member sides 24-30 facilitate a great deal of movement of the bone staple 10 when it transitions between a first material state as shown in FIG. 1A and a second material state as shown in FIG. 2A. The bone staple 10 may be made from a shape memory effect material, such as nitinol. In such a case, the geometry of the bone staple 10 in the first material state as shown in FIG. 1A will be temperature-dependent. In particular, the configuration shown in FIG. 1A may occur at room temperature and above; whereas, at a lower temperature, the bone staple 10 can be deformed to a geometric configuration such as shown in FIG. 2A, and as long as the temperature remains low enough, it will remain as shown in FIG. 2A.

In addition to the curves 34-40 in each of the bridge member sides 24-30, each of the intersections of two adjacent sides forms a respective intersection curve 42, 44, 46, 48. As shown in FIG. 1A, the intersection curves 42-48 curve outward relative to the open center portion 32, which is the opposite of the curves 34-40 of the bridge member sides 24-30. In some embodiments, intersection curves may curve inward, while the bridge member side curves are curved outward relative to an open center portion. The curves 42-48 are generally disposed at corresponding corners of the circumscribing trapezoid 14. Providing both the sides and the corners with radiused curves in the bridge member 12, provides for a great deal of linear expansion along each of the bridge member sides 24-30 when it is expanded into the second material state as shown in FIG. 2A.

In one embodiment, when the nitinol is in the first material state such as shown in FIG. 1A, the length of each of the two legs of the trapezoid 19, 21 may be approximately 13.2 millimeters (mm). Further, the length of the top 17 may be approximately 11.2 mm, and the length of the base 15 approximately 15.2 mm. Then, as shown in FIG. 2A, the bone staple 10 can be expanded at a lower temperature, such that the two legs of the trapezoid 14, now labeled 19', 21' have a length of 16 mm, the top 17' has a length of 14 mm, and the base 15' has a length of 18 mm. Similarly, the radii of the curves 34'-40' are larger than their counterparts 34-40 shown in FIG. 1A. Thus, the geometric configuration of the bridge member 12, and in particular the use of the various curved sides and corners, facilitates a great deal of linear deformation between the two material states as illustrated in FIGS. 1A and 2A.

In addition to the bridge member 12 comprising the shape memory effect material such as nitinol, each of the tines 16-22 may also comprise the same nitinol material. In fact in one method of manufacturing, the bridge member 12 and tines 16-22 are integrally formed from a single piece of nitinol using a wire electrical discharge machining (EDM) process. Immediately after such machining, the bridge member 12 and each of the tines 16-22 would lie in the same plane, for example, the plane 50 shown in FIG. 1B. After the EDM process, each of the tines 16-22 would be bent inward at some oblique angle (α) to the plane 50 that contains the bridge member 12. As illustrated in FIG. 2B, when the bone staple 10 is expanded, each of the tines 16-22 can also be bent to an angle (β) that is approximately perpendicular to the plane 50. Thus, when the bone staple 10 is returned to a warmer temperature such that it transitions to the first material state as shown in FIGS. 1A and 1B, not only will the bridge member 12 contract to try to regain the configuration shown in FIG. 1A, but each of the tines 16-22 will also try to bend inward toward the open center portion 32, as illustrated in FIG. 1B.

The circumscribing trapezoid 14 is, of course, not the only polygon that can circumscribe a bone fixation apparatus, such as contemplated by the present invention. For example, FIG. 3 shows a bone staple 52 having a generally square shaped bridge member 54, and four elongate members or tines 56, 58, 60, 62. The bridge member 54 is circumscribed by a square 64, and includes bridge member sides 66, 68, 70, 72. The bridge member 54 also includes an open center portion 74 that provides visual access to the fracture or fusion site. Each of the bridge member sides 66-72 includes a respective curve 76, 78, 80, 82, each of which curves inward toward the open center portion 74. Comparing the bone staple 52 shown in FIG. 3 to the bone staple 10 shown in FIG. 1A, it is clear that the radii of each of the curves on the bridge member sides is much smaller for the bone staple 52. In fact, the curved sides of the bridge member of other embodiments of the present invention may have a very small radius, such that it begins to approach a relatively sharp corner. In such a case, the bridge member sides may be configured in almost zig zag fashion depending on the configuration desired for the particular application.

Figure 4:
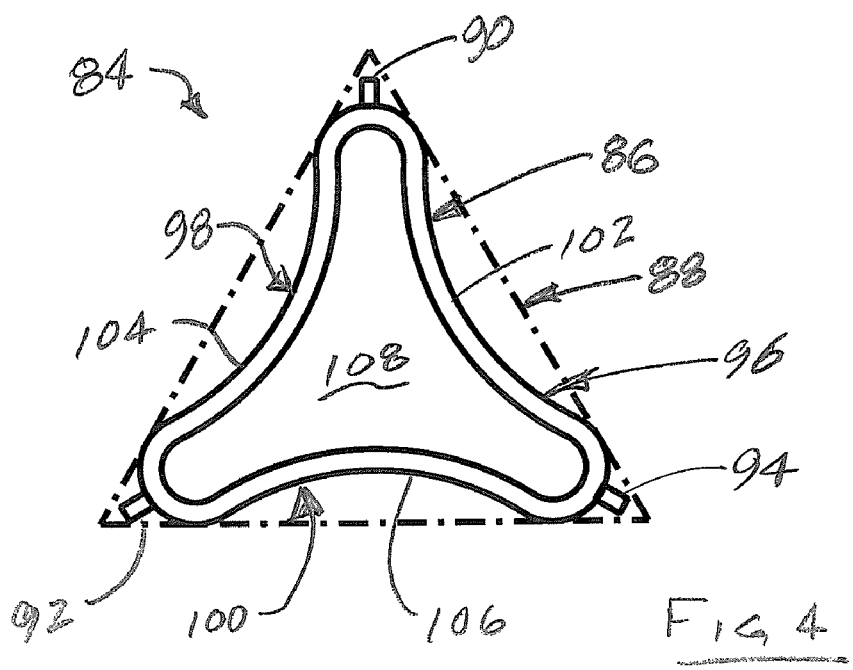
FIG. 4 is a top plan view of another embodiment of a bone fixation apparatus in accordance with the present invention.

The bone fixation apparatuses 10, 52 illustrated in FIGS. 1-3 have generally four-sided bridge members and four corresponding tines. In FIG. 4, a generally triangular shaped bone fixation device 84 is illustrated. The bone staple 84 includes a bridge member 86 that is circumscribed by a triangle 88. Although the circumscribing triangle 88 is equilateral, other shaped triangles may be used to circumscribe different bone fixation apparatuses in accordance with embodiments of the invention. In addition to the bridge member 86, the bone staple 84 includes three tines 90, 92, 94, each of which are disposed at respective corners of the circumscribing triangle 88. Similar to the other embodiments illustrated and described above, the bone staple 84 includes bridge member sides 96, 98, 100, each of which has a respective curve 102, 104, 106 that curves inward toward an open center portion 108. The triangular configuration may be particularly useful in certain fusion applications, such as a scaphoid, trapezium, trapezoid fusion of the wrist.

Figure 5A:
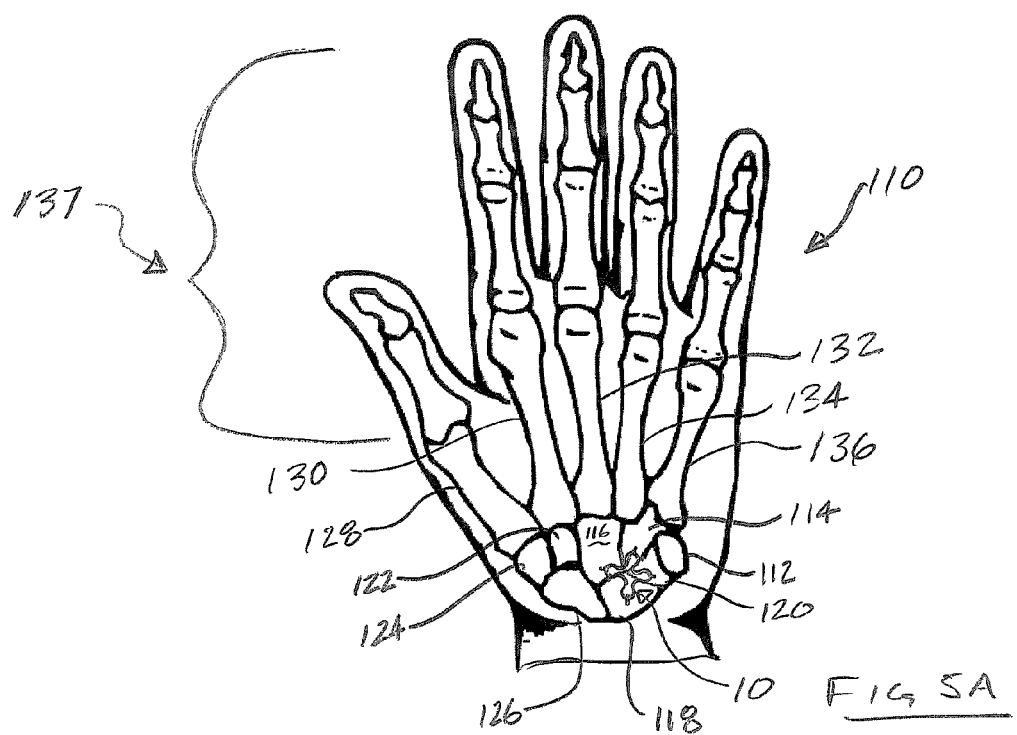
FIG. 5A is a dorsal view of a right hand having the bone fixation apparatus shown in FIG. 1A implanted in four of the wrist bones.
Figure 5B:
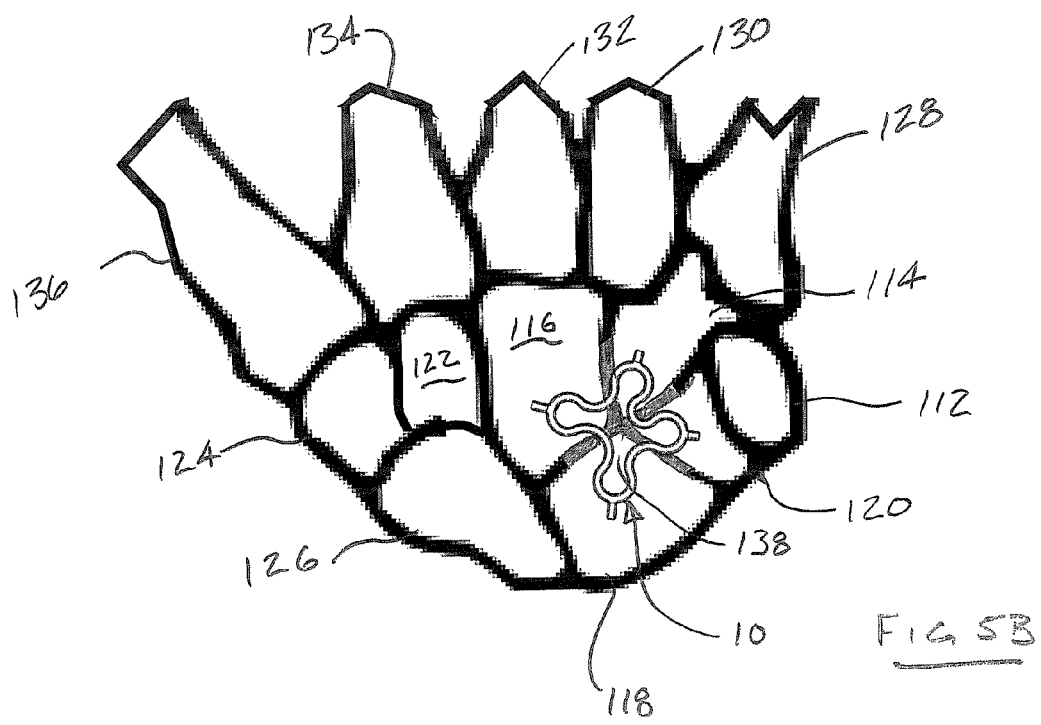
FIG. 5B is a detail view of a portion of the hand bones shown in FIG. 5A including the bone fixation apparatus implanted therein.

FIG. 5A shows a dorsal view of a right hand having some of the bones labeled to aid in the description of how a bone fixation apparatus, such as the bone staple 10 shown in FIGS. 1 and 2, can be implanted. In particular, the hand 110 includes the various bones of the wrist, such as the pisiform 112, the hamate 114, the capitate 116, the lunate 118, the triquetrum 120, the trapezoid 122, the trapezium 124, and the scaphoid 126. In addition, the first through fifth metacarpal bones 128-136 are also labeled, although, the phalanges of the upper fingers are labeled generally as 137. As shown in FIG. 5A, and in greater detail in FIG. 5B, the bone staple 10 is implanted into four of the bones of the wrist. In particular, the four tines 16-22 are each implanted into one of the hamate 114, capitate 116, lunate 118, and triquetrum 120. As clearly illustrated in FIG. 5B, the trapezoidal shape of the bone staple 10 conveniently accommodates the natural geometry of the wrist bones 114-120. In addition, a fusion site 138 is easily visible through the open portion 32 of the bone staple 10.

When the bone staple 10 is inserted into the wrist bones 114-120, it will initially be in the second material state, as illustrated in FIG. 2A. Quickly upon warming toward body temperature, the bone staple 10 will attempt to return to the configuration illustrated in FIG. 1A, as it undergoes a transition back to the first material state. Because it will be constrained by the wrist bones 114-120 into which the tines 16-22 have been inserted, it will not be able to return exactly to the geometry shown in FIG. 1A. Rather, as it attempts to contract to this shape, it will cause the tines 16-22 to pull each of the wrist bones 114-120 together toward the fusion site 138. Each of the tines 16-22 are subject to forces from each of the respective bridge member sides 24-30 as the bone staple 10 returns to the first material state, which causes the tines 16-22 to pull inward toward the fusion site 138. In this way, the bone fixation apparatuses of the present invention can be used to stabilize three or more bone pieces, and because of the curved geometry of the bridge member, apply enough force to stabilize larger fracture or fusion sites.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A bone fixation apparatus comprising:
a bridge member defining a topmost portion and forming a generally planar, closed trapezoidal figure having four sides and an open center portion, and comprising a shape memory effect material having at least two temperature-dependent states, at least a portion of each of the sides defining a curve having a respective first radius when the shape memory effect material is in a first of the temperature-dependent states, and a respective second radius larger than a corresponding first radius when the shape memory effect material is in a second of the temperature-dependent states, an intersection of each pair of the sides forming a respective intersection curve that, relative to the open center portion of the bridge member, curves in a direction opposite to the curves defined by the sides of the bridge member, the topmost portion remaining generally planar in both the first and second temperature dependent states; and
a plurality of elongate members connected to the bridge member and extending out of a plane that includes the bridge member, each of the elongate members being connected to the bridge member at an approximate intersection of a respective two of the sides, such that each of the elongate members is subject to a force from each of the respective two intersecting sides and moves toward the open center portion of the bridge member when the shape memory effect material changes from the second temperature-dependent state to the first temperature-dependent state.

2. The bone fixation apparatus of claim 1, wherein each of the elongate members comprises the shape memory effect material, each of the elongate members being generally perpendicular to the plane that includes the bridge member when the shape memory effect material is in the second temperature-dependent state, and being angled inward toward the open center portion when the shape memory effect material is in the first temperature-dependent state.

3. The bone fixation apparatus of claim 1, wherein each of the curves defined by respective sides of the bridge member curve inward toward the open center portion of the bridge member.

4. The bone fixation apparatus of claim 1, wherein each of the intersection curves is curved outward away from the open center portion of the bridge member.

5. A bone fixation apparatus comprising:
a plurality of tines configured to engage a patient's bone; and
a bridge member defining an upper boundary and comprising a shape memory effect material and forming a generally planar, closed geometric figure circumscribed by a polygon generally configured as a trapezoid having four sides, including a base, a top, and two legs, and a plurality of corners, each corner being disposed at a respective intersection of adjacent pairs of the sides, the bridge member including an open center portion and bridge member sides corresponding to respective sides of the circumscribing polygon, each of the bridge member sides curving inward toward the open center portion of the bridge member and including a respective first radius when the shape memory effect material is in a first material state, and a respective second radius larger than a corresponding first radius when the shape memory effect material is in a second material state, such that a transition of the shape memory effect material from the second material state to the first material state moves each adjacent pair of tines toward each other and each tine toward the open center portion of the bridge member while the upper boundary remains generally planar, the intersection of each pair of the bridge member sides forming a respective intersection curve that curves outward away from the open center portion of the bridge member.

6. The bone fixation apparatus of claim 5, wherein the two bridge member sides corresponding to the two legs of the circumscribing trapezoid have a first radius larger than a first radius of the bridge member side corresponding to the top of the circumscribing trapezoid and smaller than a first radius of the bridge member side corresponding to the base of the circumscribing trapezoid.

7. The bone fixation apparatus of claim 5, wherein each of the tines comprises the shape memory effect material, each of the tines being generally perpendicular to a plane that includes the circumscribing polygon when the shape memory effect material is in the second material state, and being angled inward toward the open center portion when the shape memory effect material is in the first material state.

8. A bone fixation apparatus comprising:
a topmost planar member comprising a shape memory effect material and circumscribed by a trapezoid, the planar member having four corners each defining a radius that curves outward away from a center of the planar member and four sides each curving inward toward the center of the planar member, each of the sides defining a respective first radius when the planar member is in a first material state and a respective second radius larger than a corresponding first radius when the planar member is in a second material state; and
four elongate members respectively disposed at the four corners of the planar member and extending outwardly therefrom, each of the elongate members being subject to a force from two corresponding sides of the planar member which remains generally planar and urges the respective elongate member toward the center of the planar member when the planar member changes from the second material state to the first material state.

\* \* \* \* \*